(12) United States Patent
Adams

(10) Patent No.: US 7,858,026 B2
(45) Date of Patent: Dec. 28, 2010

(54) DETECTION OF STERILISATION VAPOUR CONDENSATION POINT

(75) Inventor: Nicholas Mark Turner Adams, Clanville (GB)

(73) Assignee: Bioquell UK Limited, Hampshire (GB)

( * ) Notice: Subject to any disclaimer, the term of this patent is extended or adjusted under 35 U.S.C. 154(b) by 159 days.

(21) Appl. No.: 11/718,595

(22) PCT Filed: Jul. 27, 2006

(86) PCT No.: PCT/GB2006/002817

§ 371 (c)(1),
(2), (4) Date: May 3, 2007

(87) PCT Pub. No.: WO2007/012866

PCT Pub. Date: Feb. 1, 2007

(65) Prior Publication Data

US 2009/0060781 A1    Mar. 5, 2009

(30) Foreign Application Priority Data

Jul. 28, 2005    (GB) .................................. 0515569.2

(51) Int. Cl.
A61L 2/24    (2006.01)
A61L 9/00    (2006.01)

(52) U.S. Cl. ............................................. 422/3; 422/29

(58) Field of Classification Search ..................... 422/3, 422/29

See application file for complete search history.

(56) References Cited

U.S. PATENT DOCUMENTS 7,014,813 B1    3/2006  Watling et al.
7,025,932 B2    4/2006  Martin et al.
2003/0063997 A1*  4/2003  Fryer et al. ..................... 422/3

FOREIGN PATENT DOCUMENTS

| EP | 1 016 421 A1 | 7/2000 |
| EP | 1 166 802 A2 | 1/2002 |
| EP | 1 378 248 A1 | 1/2004 |
| GB | 2 354 443 A  | 3/2001 |

(Continued)

OTHER PUBLICATIONS

David Watling et al., *Theoretical Analysis of the Condensation of Hydrogen Peroxide Gas and Water Vapour as Used in Surface Decontamination*, PDA Journal of Pharmaceutical Science and Technology, vol. 56, No. 6, Nov./Dec. 2002, pp. 291-299.

(Continued)

*Primary Examiner*—Sean E Conley
*Assistant Examiner*—Kevin C Joyner
(74) *Attorney, Agent, or Firm*—Workman Nydegger

(57) ABSTRACT

A method of detecting bacterial kill using a vaporized sterilant includes the steps of generating a sterilant/water vapour and supplying the vapour to a sealed space to be sterilized. The supply of sterilant/water vapour is continued to raise the concentration of the sterilant in the sealed space, and the concentration of the sterilant in the vapour is monitored to determine when the rate of change of the concentration falls to a predetermined minimal level indicating that condensation has occurred resulting in kill of any bacteria present in the space. Supply of sterilant/water vapour to the space is then terminated.

11 Claims, 3 Drawing Sheets

FOREIGN PATENT DOCUMENTS

WO     WO 03/082355 A1     10/2003

OTHER PUBLICATIONS

M. Kokubo et al., *Resistance of Common Environmental spores of the Genus Bacillus to Vapor Hydrogen Peroxide*, PDA Journal of Pharmaceutical Science and Technology, vol. 52, No. 5, Sep./Oct. 1998, pp. 228-231.

Block, *Disinfection, Sterilization, and Preservation*, 5th Edition, published 2001, Lippincott Williams & Wilkins, pp. 22, ISBN 0-683-30740-1.

Russell, *Principles and Practice of Disinfection, Preservation and Sterilisation*, 3rd Edition, published 1999, Hugo and Ayliffe, Blackwell Science, pp. 708, ISBN 0-321-04194-3.

Block, *Disinfection, Sterilization, and Preservation*, 5th Edition, published 2001, Lippincott Williams & Wilkins, pp. 82-83, ISBN 0-683-30740-1.

D. Walting, *Why Bother to Understand the Behaviour of Flash Evaporated Hydrogen Peroxide?*, Presentation, ISPE Barrier Conference, Washington, May 2004.

\* cited by examiner

DETECTION OF STERILISATION VAPOUR CONDENSATION POINT

BACKGROUND OF THE INVENTION

1. Field of the Invention

The present invention describes a technique to determine when a gaseous bio-decontamination process has been successful.

2. Present State of the Art

The problem addressed by this invention is a method of establishing when gaseous bio-decontamination of a chamber has been successfully completed. The most commonly used technique to show that a bio-decontamination has been achieved is with Biological Indicators (BIs) (see Disinfection, Sterilization, and Preservation, 5$^{th}$ Edition. Block, Lippincott Williams & Wilkins. p 22, and Principles and Practice of Disinfection, Preservation and Sterilization, 3$^{rd}$ Edition. Russell, Hugo and Ayliffe. Blackwell Science. p 708). These are small coupons, usually about 10 mm in diameter, manufactured from stainless steel and inoculated with about one million bacterial spores. Endospores are chosen for this purpose because it is generally accepted that they are one of the more resistant organisms. BIs are placed around the chamber to be decontaminated and then removed at the end of the gassing period and either placed into a growth media and then incubated to see if any of the spores are still viable, or placed into buffer solution and then the number of viable spores are estimated. The use of BIs is time consuming and when they are placed into growth media the results are not generally considered to be definitive for at least seven days. The process of estimating the number of viable spores after placing the BIs in buffer solution is labour intensive and again the results will not be immediately available.

As a result of the time taken to establish if a gaseous bio-decontamination has been successful (because of the delay caused by the analysis methods) it is common practice to ensure gross overkill by using excessive amounts of gas and exposing the chamber for periods which are longer than necessary. In the event of a failure to achieve a kill of the spores on the BI, the process would have to be repeated, thus doubling the time for the bio-decontamination process. Long exposure to excessive amounts of gas increases the time taken to remove the gas from the chamber at the end of the process thus further increasing the overall cycle time.

A method of establishing the point in the gassing process when the micro-organisms have been killed would be of benefit because it would shorten the cycle time and also remove the uncertainty that the process has been successful.

If a population of micro-organisms are subjected to a consistent stress level sufficient to cause kill then it is generally accepted that the time taken to reduce the viable population by a factor of 10 will always be the same. Thus if the initial population is 1,000,000 and this reduces to 100,000 in 2 minutes then in a further 2 minutes the viable population will fall to 10,000. The time taken to achieve a 10 fold reduction, sometimes referred to as a 1 log reduction is called the 'D' value (see Disinfection, Sterilization, and Preservation, 5$^{th}$ Edition. Block, Lippincott Williams & Wilkins. p 82-83). The death kinetics of micro-organisms are not always strictly linear, but the 'D' value concept is broadly accepted in the field of microbiology.

Hydrogen peroxide vapour has become the decontaminant of choice for gaseous bio-decontamination in the Pharmaceutical Industry (see Lysford J. ISPE Barrier Conference, May 2004, Washington) because the process is rapid, reliable and leaves no residues. It is also environmentally friendly because the vapour can be converted to water and oxygen at the end of the process. It has been established that once the correct stress level has been achieved the 'D' value for *Geoacillus stearothermophilus* endospores is less than 2 minutes (see Resistance of common environmental spores of the genus *Bacillus* to vapour hydrogen peroxide. Kokubo M. et al. PDA J. of Phar. Sci. & Tech. Vol. 52, No. 5. September/October 1998 p 228-231). Thus, if the test population is 1,000,000 organisms then bio-decontamination would be achieved in 12 minutes once the correct stress level is established. For the purposes of this discussion we will consider how to find the point in a gaseous hydrogen peroxide decontamination cycle when the required stress level has been achieved, but identical arguments apply to other gaseous bio-decontamination processes and other micro-organisms.

SUMMARY OF THE INVENTION

This invention provides a method of detecting bacterial kill using a vaporized sterilant comprising the steps of generating a sterilant/water vapour and supplying the vapour in a sealed space to be sterilized, continuing to supply the sterilant vapour to raise the concentration of sterilant in the sealed space, monitoring concentration of the sterilant in the vapour, determining when the rate of change of concentration falls to a predetermined minimal level indicating that condensation has occurred resulting in kill of any bacteria present in the space and terminating supply of sterilant vapour.

The predetermined minimal rate of change of concentration of the sterilant/water vapour may be a positive or a negative rate of change.

In any of the above methods the temperature of the atmosphere in the enclosed space may be monitored and the supply of sterilant/water vapour to the sealed space is continued whilst the temperature rises until the rate of change of concentration falls to said predetermined level.

Also in any of the above methods the sterilant/water vapour may be supplied to the chamber to cause a multiple number of atmosphere changes in the chamber in raising the concentration of sterilant in the chamber.

BRIEF DESCRIPTION OF THE DRAWINGS

The following is a description of some specific embodiments of the invention, reference being made to the accompanying drawings in which.

DETAILED DESCRIPTION OF THE PREFERRED EMBODIMENTS

Figure 1:
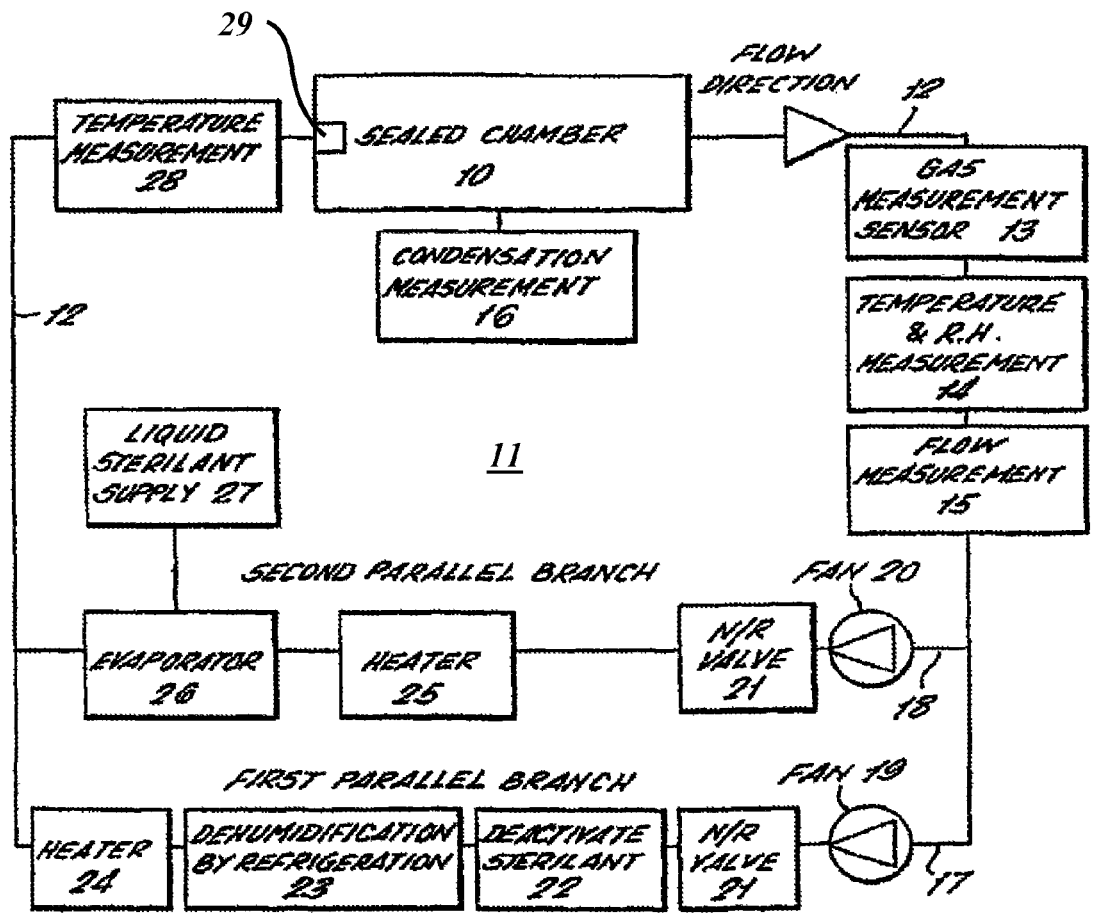
FIG. 1 is a diagrammatic view of a sealed chamber and a sterilization circuit connected to the chamber for sterilizing the interior and contents of the chamber using a gas carrying an aqueous vapour of a liquid sterilant, the circuit having two pumps or fans.

The apparatus comprises a sealed chamber 10, and an apparatus included generally at 11 incorporating a dual circuit for dehumidification, sterilizing and aeration of the sealed chamber 10. A carrier gas, i.e. air, and a sterilizing gas or gases are drawn from the sealed chamber to the apparatus through sealed connections fluidly connecting the chamber to the apparatus.

The apparatus comprises a gas flow circuit 12 containing in series, a gas monitor 13 a temperature and humidity monitor 14 and a flow measurement device 15. The gas monitor is an electrochemical cell giving a signal proportional to the gas concentration or can be a near infra-red spectrophotometer. Suitable temperature and humidity sensors 14 are commonly available as a single commercial instrument, and any such device that is resistant to hydrogen peroxide vapour would be suitable for this application. The most suitable, and cost effective, flow measurement 15 system is based on the measurement of the pressure difference across a restriction in the flow, typically an orifice plate.

Attached to the sealed chamber is a condensation measurement system 16. Proprietary systems are not readily available, but techniques have been developed that rely on the change in reflectivity of a surface in the chamber to indicate the mass of condensate that has formed. Alternative techniques that may include measuring equipment may be mounted on the outside of the chamber.

Downstream of the flow measurement system the circuit divides into two parallel branches 17, 18. Each branch has a fan 19, 20 and each fan has an associated non-return valve 21. As the pressure required to force the circulating gas round the system is generally not large then a standard variable speed centrifugal fan would suffice for such an application. The non-return valves are required to ensure that there is no back flow in the wrong direction. Simple flap devices are all that is required in this application. In the first parallel branch 17 is a system 22 to deactivate and remove the sterilant gas or gases from the carrier gas, and a further system 23 to dehumidify the gas stream. Downstream of the dehumidification system is a heater 24 to raise the circulating gas temperature. The deactivating system for the sterilant gas comprises a catalyst bed, which decomposes the vapour to harmless components. For hydrogen peroxide gas a suitable catalyst would be ruthenium on inert pellets which decomposes the gas to water vapour and oxygen.

A desiccant dryer may perform the dehumidification process, but a more suitable technique would be to reduce the gas temperature using a refrigeration system. The reduction in temperature causes the water vapour to condense with the products of decomposition. The resulting condensate and decomposition products may then be pumped away. It is necessary to raise the circulating gas temperature after dehumidification and an electric heater 24 or other heating means is placed downstream of the dehumidifier for the purpose.

In the second parallel branch is a heater 25 to raise the gas temperature prior to entering an evaporator 26, in which the liquid sterilant is turned to vapour by heating. A liquid sterilant supply 27 controls the liquid flow to the evaporator.

The heater 25 may be of a similar construction to the other heater 24. The evaporator is a flash evaporator in which the liquid sterilant is evaporated by dropping under gravity a stream of liquid onto a heated surface. The flow of liquid from the sterilant supply is fed onto the heated surface at a selected rate by using a variable speed pump, which is controlled from a flow measuring system. The gas temperature entering the sealed chamber 10 is measured at 28 using a standard temperature probe. Gas entry to the chamber 10 is through a gas distribution system 29 including a rotating nozzle arrangement which projects gas at high temperature and velocity to every part of the chamber. In addition a system for control gas pressure in the circuit to raise or reduce pressure as required is provided.

The method of sterilizing the enclosure using the above apparatus comprises the steps of reducing the relative humidity in the enclosure, then circulating a carrier gas containing an aqueous vapour of the sterilizing gas or gases, and finally removing the sterilizing gas or gases.

The first phase of reducing the relative humidity is essential to ensure that all of the surfaces inside the sealable chamber are at the same state of dryness. During the second phase the sterilizing gas or gases are delivered to the sealed chamber at an elevated temperature in order that as much as possible of the sterilant may be transported into the sealed chamber. The third and final stage is the removal of the sterilant gas or gases by passing clean dry carrier gas into the sealed chamber to carry away the active gas or gases.

The first phase of reducing the humidity may be in two parts, the first to reduce the relative humidity to a pre-selected value, and a second part to hold the humidity at that value to allow the sealed chamber to come to a stable state.

Similarly the second phase when the gas or gases are passed into the sealed chamber is in two parts. The first part is to raise the concentration and generate the required level of condensation on the surfaces, with a second dwell part to allow the condensate to act the microorganisms. The level of condensation is measured during the first part of the second phase and when it has reached the required level the supply of sterilizing gas or gases is stopped but the carrier gas with the associated saturated vapours continues to circulate. The circulating saturated vapour prevents evaporation of the layer of condensation allowing the liquid film to act on the microorganisms.

During the third and final phase of the sterilization cycle the carrier gas together with the sterilizing gas or gases is circulated through a system to render the active gases harmless, so that it may be taken away, whilst at the same time removing the water vapour in a dehumidifier. The clean carrier gas is then returned to the sealed chamber where it gathers more of the active gas or gases thus further reducing to the level of the active ingredients. This process continues until the active ingredients have been reduced to an acceptable level.

It has been shown (see Watling ISPE Barrier Conference May 2000, Washington) that the critical stress level on the micro-organisms is achieved once a very fine layer of condensation has formed. This layer of condensation is probably of the order of 1 to 2 microns and may be invisible to the naked eye. Because of the difficulty in sensing such a fine layer of condensation there are no generally available commercial instruments available of sufficient accuracy to indicate when this layer has formed. The relationship between hydrogen peroxide and water vapours and their condensation have been analyzed by Watling (see Theoretical analysis of the condensation of hydrogen peroxide gas and water vapour as used in surface decontamination. Watling et al. PDA J. of Phar. Sci & Tech. Vol. 56, No. 6 November/December 2002 p 291-299). The equations developed by Watling suggest that the first bead of condensation is likely to be at a higher concentration than the evaporated liquid leading to a high gas concentration that falls once the layer of condensation increases. This high level of gas concentration will only occur in small chambers where the temperature of the surfaces on which the condensation forms are equal and the temperature of the gas is significantly higher than the walls of the chamber. In larger chambers where the gas will cool in the air space there is generally no peak of the gas condensation at the start of the condensation process.

The concentration of the hydrogen peroxide gas in the chamber will increase as the delivered gas displaces the mixture of air/air and gas in the chamber. The standard equation used to calculate the rate of rise of gas concentration is derived from:

$$\text{proportion of Air removed} = 1 - e^{-N}$$

Where N is the number of air changes, and is the volume of the chamber divided by the total volume of air supplied up to a specified time.

Hence the concentration of the hydrogen peroxide in the chamber will be given by:

$$\text{Concentration} = C\{1 - e^{-N}\}$$

(see Theoretical analysis of the condensation of hydrogen peroxide gas and water vapour as used in surface decontamination. Watling et al. PDA J. of Phar. Sci & Tech. Vol. 56, No. 6 November/December 2002 p 291-299).

Where C is the concentration of the delivered gas.

Figure 2:
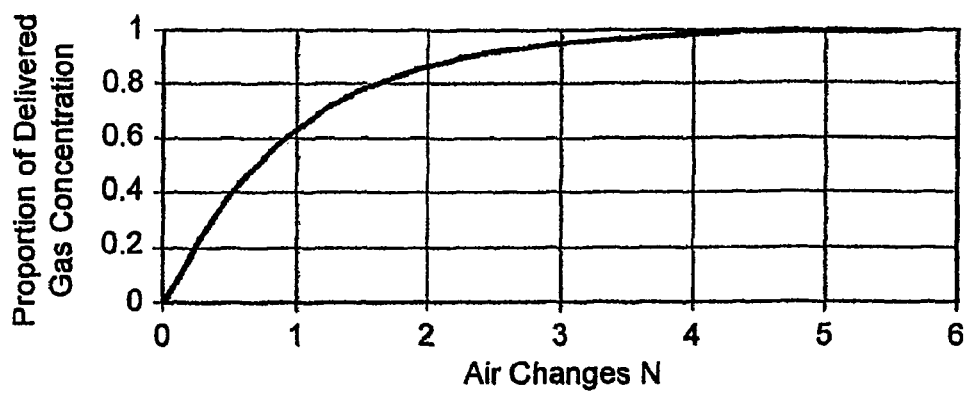
FIG. 2 is a graph depicting a proportion of delivered gas concentration in the chamber in a practical example.

Reference is now made to FIG. 2 of the drawings which is a graph of gas concentration in the chamber. More specifically it is a plot of the proportion of delivered gas concentration against air changes in the chamber.

It will be noted from the graph that the gas concentration in the chamber will rise to the delivered concentration after about 6 air changes. For a gaseous hydrogen peroxide bio-decontamination to be effective it is necessary to deliver a gas concentration to the chamber that is higher than the saturated vapour pressure. As suggested earlier this requires that the temperature of the delivered gas is higher than the temperature inside the chamber. In practice the hydrogen peroxide gas is generated by evaporating an-aqueous solution in such a way as to produce a vapour with the same weight concentration as the source liquid.

Providing the concentration of the gas supplied to the chamber is above the saturated vapour pressure at the chamber temperature then condensation will form in equilibrium with the vapour phase. The equilibrium vapour pressure of the hydrogen peroxide will depend on the temperature inside the chamber, the concentration of the evaporated aqueous hydrogen peroxide solution and the water content of the air inside the chamber at the start of the process. The gas concentration will therefore not reach the concentration of the supplied gas, but instead will plateau at the saturated vapour pressure. This flattening indicates that condensation has formed and that the stress level on the micro-organisms has reached a level at which rapid and reliable kill occurs. Because of the difficulty of measuring with the required degree of accuracy the water an hydrogen peroxide vapour concentration inside the chamber it is difficult to find the point at which condensation occurs from the instrumentation. A change of a 2.5 percentage points in the RH at 25° C. will alter the hydrogen peroxide saturated vapour concentration by about 10%.

Figure 3:
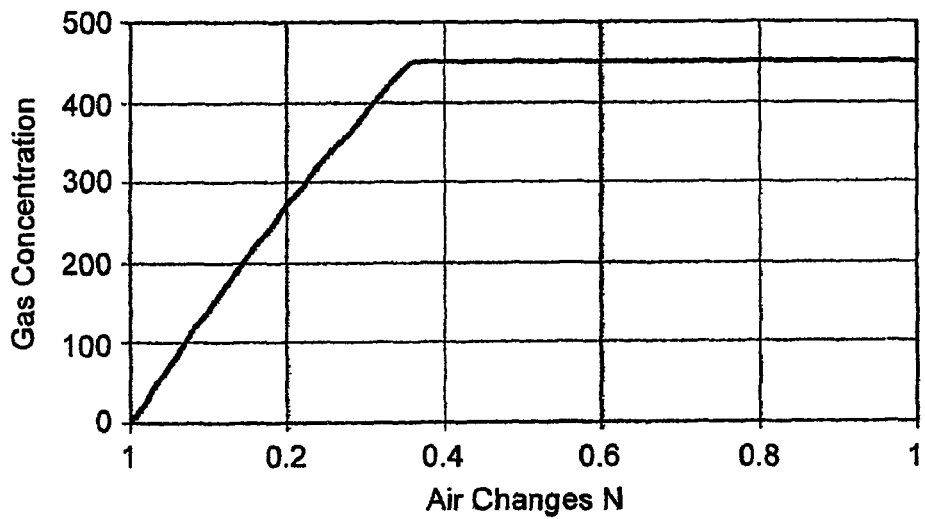
FIG. 3 is a graph of gas concentration plotted against air change in ideal gas conditions.

In practice the concentration of the hydrogen peroxide gas delivered to the chamber will be of the order of 3500 ppm or higher, and the saturated vapour pressure will be bout 450 ppm. Thus under ideal gas conditions it would be expected that the gas concentration would be similar to that shown in FIG. 2 which is a graph depicting an ideal gas concentration curve and more specifically relates gas concentration to air changes in the chamber. But because of small variations in the temperature and the difficulty in achieving perfect mixing of the gas entering the chamber the gas concentration profile will show a transitional phase. FIG. 3 is a plot showing the gas concentration profile from an actual room gassing and shows the typical transition between the increase in concentration at the start of gassing and a flattening of the curve once condensation has started.

Figure 4:
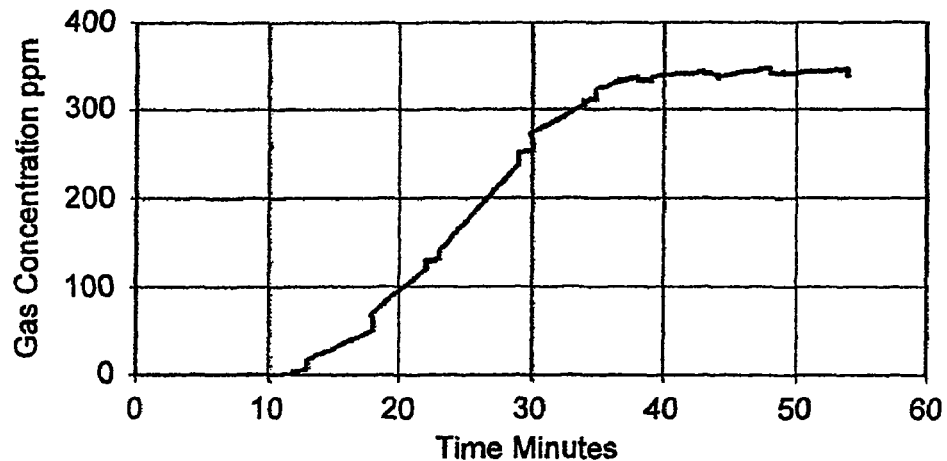
FIG. 4 is a plot showing gas concentration against actual room gassing illustrating initial increase in concentration at the start of gassing and flattening of the curve once condensation has started.

It is possible to calculate knowing the room size, liquid evaporation rate, the starting RH in the chamber, and the chamber temperature the theoretical gas concentration curve. This calculation has been performed the result of which is shown in the graph of FIG. 4 together with the measured gas concentration.

It will be noted in the above plot that the actual gas concentration curve flattens over 40 minutes indicating that condensation has occurred; this lags the theoretically predicted gas concentration due to imperfect mixing of the gas and temperature variations inside the chamber.

The flattening of the curve shows that condensation has started and hence the required stress level that will kill micro-organisms has been attained. Theoretically if the gassing cycle is continued for a further period of time equal to six times the 'D' value then bio-decontamination should have happened. In practice kill may occur, especially in rooms and large chambers, prior to this flattening because during the transitional phase condensation preferentially forms on the micro-organism (see ISPE Barrier Isolation Technology Forum Arlington 2002, Watling, Why bother to understand the behavior of flash evaporated hydrogen peroxide?). It is, however, sensible to maintain the critical level of condensation after the curve has flattened for a period of time equivalent to six times the D value to ensure that kill has taken place. In smaller chambers of say up to 10 m$^3$ the gas concentration will rise very quickly, frequently reaching saturation in a shorter period than the equivalent of six times the D value, and hence it is essential in these smaller chambers to maintain the saturated state, and hence the flat gas concentration curve, for a sufficient period of time to achieve the required kill. The observation of the flattening of the gas concentration curve may be conducted either visually or by using some logging computer software that will fit the recorded data to a curve and then find the moment when the gas concentration has ceased to rise. This will give the moment when condensation must have reached the critical kill level.

Two tests were performed measuring the gas concentration in a room and removing Geobacillus stearothermophilus biological indicators at timed intervals to establish the point in time when kill was achieved. The room had a volume of approximately 110 m$^3$ and the hydrogen peroxide evaporation rate was 12 g/minute. The initial temperature in the room was 23° C. with a starting relative humidity of 38.5% and the ambient temperature was 18.6° C. By working through glove ports in one of the room's windows the BIs were placed in growth media at timed intervals of 5 minutes starting 20 minutes after the start of gassing. After removal the BIs were placed in growth media and examined for growth each day for 14 days. Turbidity of the growth media was seen for the samples that were removed for the first 30 minutes of the gassing period, thereafter there was no growth.

Figure 5:
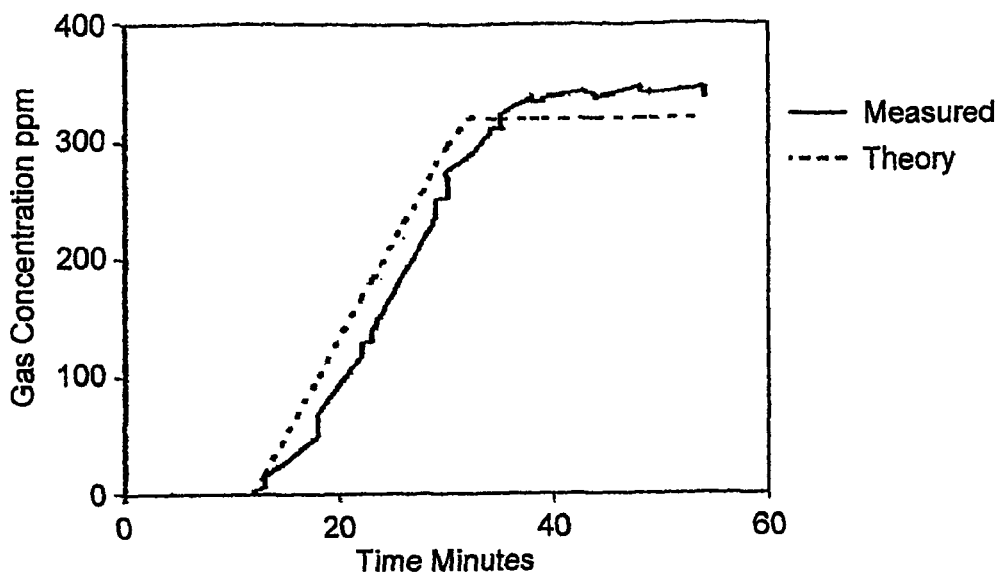
FIG. 5 is a similar graph to FIG. 3 combining both theoretical and measured gas concentration.
Figure 6:
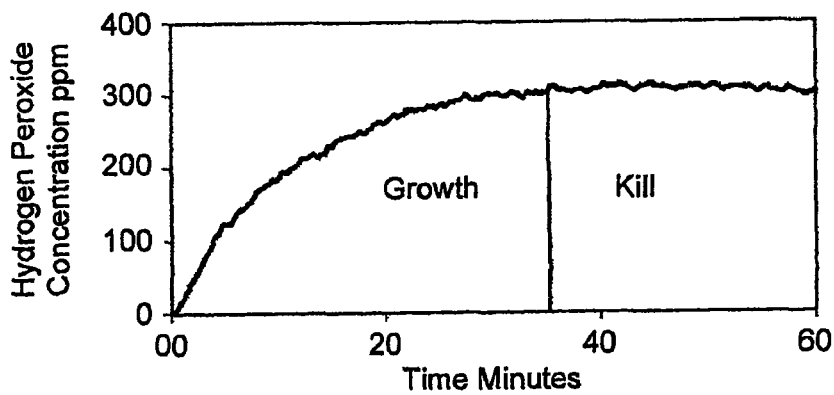
FIGS. 6 and 7 are graphs showing test results obtained from measuring the gas concentration in a room and removing particular biological indicators at timed intervals when kill is achieved.
Figure 7:
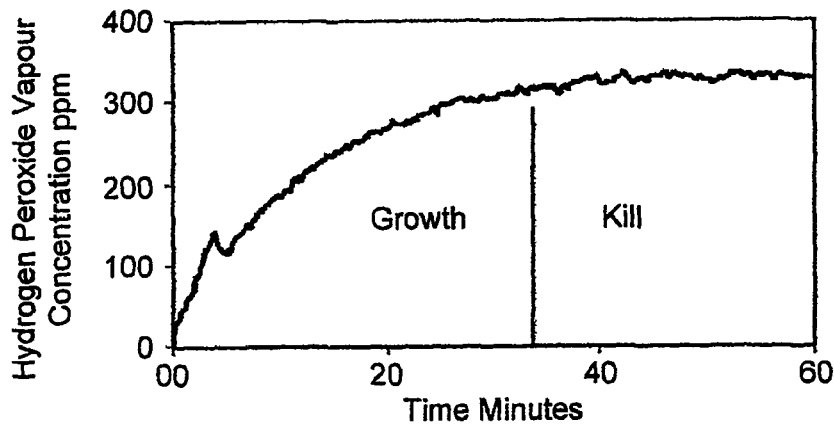

The results are shown graphically in FIGS. 5 and 6. The Kill and Growth areas are marked on each plot, showing that once the curve has substantially flattened kill has been achieved. Any additional time after flattening will give added security to the kill cycle.

The invention claimed is:

1. A method of detecting bacterial kill using a vaporized sterilant comprising the steps of:

generating a sterilant/water vapour and supplying the vapour in a sealed space to be sterilized, continuing to supply the sterilant/water vapour to raise a concentration of the sterilant in the sealed spaced, monitoring concentration of the sterilant in the vapour by measuring the concentration of sterilant in the vapour, determining from said measured concentration values when a rate of change of the concentration of the sterilant falls to a predetermined minimal level indicating that condensation of the vapour has occurred resulting in kill of any bacteria present in the space, and terminating supply of the sterilant/water vapour.

2. A method as claimed in claim 1, wherein said predetermined minimal level of the rate of change of the concentration of the sterilant is a positive rate of change.

3. A method as claimed in claim 2, wherein a temperature of an atmosphere in the enclosed space is monitored and the supply of sterilant/water vapour to the sealed space is continued whilst the temperature rises until the rate of change of the concentration of the sterilant falls to said predetermined minimal level.

4. A method as claimed in claim 2, wherein the sterilant/water vapour is supplied to the chamber to cause a multiple number of atmosphere changes in the chamber in raising the concentration of the sterilant in the chamber.

5. A method as claimed in claim 1, wherein the predetermined minimal level of the rate of change of the concentration of the sterilant is a negative rate of change.

6. A method as claimed in claim 5, wherein a temperature of an atmosphere in the enclosed space is monitored and the supply of sterilant/water vapour to the sealed space is continued whilst the temperature rises until the rate of change of the concentration of the sterilant falls to said predetermined minimal level.

7. A method as claimed in claim 5, wherein the sterilant/water vapour is supplied to the chamber to cause a multiple number of atmosphere changes in the chamber in raising the concentration of the sterilant in the chamber.

8. A method as claimed in claim 1, wherein a temperature of an atmosphere in the enclosed space is monitored and the supply of sterilant/water vapour to the sealed space is continued whilst the temperature rises until the rate of change of the concentration of the sterilant falls to said predetermined minimal level.

9. A method as claimed in claim 8, wherein the sterilant/water vapour is supplied to the chamber to cause a multiple number of atmosphere changes in the chamber in raising the concentration of the sterilant in the chamber.

10. A method as claimed in claim 1, wherein the sterilant/water vapour is supplied to the chamber to cause a multiple number of atmosphere changes in the chamber in raising the concentration of the sterilant in the chamber.

11. A method of detecting bacterial kill using a vaporized sterilant comprising the steps of:

generating a sterilant/water vapour and supplying the vapour in a sealed space to be sterilized;

continuing to supply the sterilant/water vapour to raise a concentration of the sterilant in the sealed spaced;

monitoring concentration of the sterilant in the vapour by directly measuring the concentration of sterilant in the vapour;

determining from the measured concentration values when a rate of change of the concentration of the sterilant falls to a predetermined minimal level indicating that condensation of the vapour has occurred in the sealed space; and terminating supply of the sterilant/water vapour when the rate of change of the concentration of the sterilant falls to the predetermined minimal level.

* * * * *

UNITED STATES PATENT AND TRADEMARK OFFICE
CERTIFICATE OF CORRECTION

| | | |
|---|---|---|
| PATENT NO. | : 7,858,026 B2 | Page 1 of 1 |
| APPLICATION NO. | : 11/718595 | |
| DATED | : December 28, 2010 | |
| INVENTOR(S) | : Adams | |

It is certified that error appears in the above-identified patent and that said Letters Patent is hereby corrected as shown below:

Column 1
Line 41, change "BI" to --BIs--

Column 3
Line 12, change "gas monitor 13" to --gas monitor 13,--

Column 4
Line 30, change "act the microorganisms" to --act on the microorganisms--

Column 5
Line 38, change "an-aqueous" to --an aqueous--
Line 55, change "an hydrogen" to --and hydrogen--
Line 62, change "bout" to --about--

Column 7
Line 4, change "spaced" to --space--

Column 8
Line 24, change "spaced" to --space--

Signed and Sealed this

Eighteenth Day of October, 2011

David J. Kappos
*Director of the United States Patent and Trademark Office*